(12) United States Patent
Greeson et al.

(10) Patent No.: US 7,820,187 B2
(45) Date of Patent: Oct. 26, 2010

(54) METHOD AND MIXTURE FOR PROTECTING ANIMALS AGAINST PESTS

(75) Inventors: John S. Greeson, Dexter, NM (US); Eric H. Bonewitz, Overland Park, KS (US)

(73) Assignee: Dairy Solutions, LLC, Dexter, NM (US)

( * ) Notice: Subject to any disclaimer, the term of this patent is extended or adjusted under 35 U.S.C. 154(b) by 977 days.

(21) Appl. No.: 10/659,840

(22) Filed: Sep. 11, 2003

(65) Prior Publication Data

US 2004/0047889 A1    Mar. 11, 2004

Related U.S. Application Data

(63) Continuation-in-part of application No. 09/844,316, filed on Apr. 26, 2001, now abandoned.

(51) Int. Cl.
*A01N 25/04* (2006.01)
*A01N 53/02* (2006.01)

(52) U.S. Cl. .................. 424/405; 424/59; 424/406; 514/65; 514/75; 514/521; 514/531; 514/875; 514/919

(58) Field of Classification Search ........... None
See application file for complete search history.

(56) References Cited

U.S. PATENT DOCUMENTS

| | | | | |
|---|---|---|---|---|
| 2,988,473 A | * | 6/1961 | Mallis et al. .............. 514/63 |
| 3,393,990 A | * | 7/1968 | Geary .................. 504/361 |
| 4,176,076 A | * | 11/1979 | Waldstein ............. 508/195 |
| 4,316,914 A | * | 2/1982 | Coffee et al. ............ 514/531 |
| 4,902,510 A | * | 2/1990 | Garden .................. 424/405 |
| 5,104,659 A | * | 4/1992 | Fishbein et al. ........... 424/411 |
| 6,455,504 B1 | * | 9/2002 | Lewer et al. ............. 514/28 |

OTHER PUBLICATIONS

Velcon-Centistokes to Saybolt Universal Seconds Conversion—2003.*

* cited by examiner

*Primary Examiner*—Neil Levy
(74) *Attorney, Agent, or Firm*—Robert W. Becker; Robert Becker & Associates

(57) ABSTRACT

A mixture for application on an animal to provide barrier protection against insects, parasites, arachnids and/or other arthropods, and ectoparasites, and in general viruses, bacteria and/or other microorganisms is provided. The mixture includes a carrier or combination of carriers, especially mineral oil, that at least after application has an absolute or resultant viscosity of from 100 to 1200, and especially greater than 120, and especially 300 to 650 S.U.S. The mixture also includes an insecticide, ectoparasitide, insect or other arthropod growth regulator (IGR), viricide, bacteriacide and/or bacteriostatic compound that is blended with the carrier and that acts non-systemically. The mixture contains essentially no surfactant, emulsifier, or emulsifying agent, either in solution or suspension.

16 Claims, No Drawings

METHOD AND MIXTURE FOR PROTECTING ANIMALS AGAINST PESTS

CROSS-REFERENCE TO RELATED APPLICATIONS

This application is a continuation-in-part of pending application Ser. No. 09/844,316 filed Apr. 26, 2001 now abanndoned.

BACKGROUND OF THE INVENTION

The present invention relates to a mixture for application on an animal to provide an essentially non-evaporative, non-absorbent and not water soluble barrier protection against the negative effects of external pests. The present invention also relates to a method of protecting animals using such a mixture.

For application to animals, it is known to blend active ingredients such as insecticides, ectoparasitides and endoparasitides with oil or water based carriers. These carriers have a low viscosity, based on cost and in particular the ability of such a carrier to penetrate below the hair of an animal.

The carriers of heretofore known mixtures have a viscosity that allows the carrier to penetrate below the animal's hair since many active ingredients degrade substantially in UV light and therefore lose their efficacy relatively quickly. By using a low viscosity oil or water, the known products will penetrate under the surface hair of the animal and will thus reside on the animal out of the sunlight, with the animal's hair shading the product. This extends the life of the active ingredient on the animal. A low viscosity oil or water, once applied and below the surface hair and on the skin of the animal, also enables the spread of the oil to increase the surface area of the animal being covered by the active ingredient. While low viscosity improves the spread of these products, negatively they are very susceptible to mechanical water migration and/or they wash off in either rain storms or when water dosing of animals is implemented for animal cooling or cleaning purposes.

An additional disadvantage of low viscosity oils is in their inherent low weight or mass. Because of this, when applied through sprayers or equipment such as that described in U.S. Pat. No. 6,230,660, they are inherently susceptible to even slight wind currents. When wind is present as the host animal is sprayed, much or all of the discharged mixture may be lost to the atmosphere as a result of wind currents and fail to be applied to the host animal in proper amount or even at all. This results in either or both increased usage of the applied mixture, which is economically inefficient, and/or insufficient application of the mixture to the animal, in which case intended results may be substandard or even nonexistent.

Typically these products have been and are designed and manufactured for the treatment of horn flies, stable flies, ticks and other external blood sucking pests, where ½ to 5 ounces of product is dispensed every 2 to 6 weeks along the center of the back from the tail head to the shoulders. This volume of product is sufficient to overcome losses to follicle and dermal absorption and half-life or other degradation of the active ingredients, the remainder then resting on the skin below the hair line where the above mentioned pests would come in contact with it during feeding.

A drawback of the heretofore known carriers is that they are not optimally effective in making the active ingredient available for the required contact with all pests of concern. An example of this would be house flies that are non blood sucking and feed, for example, on debris upon animals or upon sites upon the animal where saliva or mucous are present and secreted such as the eyes, nostrils, mouth, and vulva. Furthermore, this allows transdermal absorption of the active ingredient into the animal and hence possibly its entry into the human food chain.

Examples of heretofore known compositions include U.S. Pat. Nos. 5,134,132 (Matthewson), 4,762,718 (Marks Sr.), 6,071,857 (Vogt et al.), 4,668,666 (Allan et al.) and 4,568,541 (Dorn et al). Further known compositions are described in U.S. Pat. Nos. 6,001,384 (Jeannin) and 6,524,594 (Santora), and U.S. Pat. No. 2002/00 34489 (Weigland). Unfortunately, Jeannin, as do several of the other earlier patents, operate systemically, thus potentially adversely affecting the quality of any derived human or pet food product. Furthermore, among others, Vogt, Santora and Weigland contain surfactants or emulsifiers, which make them absorbable and/or water soluble, and thus subject to the aforementioned drawbacks. Additionally, since surfactants by their very nature lower the surface tension of the solution in which they are incorporated, their presence greatly increases the potential for transdermal absorption into the treated animal and, therefore, the potential for the active ingredient to enter the food chain of either humans or other animals.

It is therefore an object of the present invention to provide an effective animal barrier protection mixture that remains on surface relatively unaffected by follicle and dermal penetration or absorption and resistant to mechanical water migration.

SUMMARY OF THE INVENTION

The method and mixture of the present invention for application on an animal to provide protection against pests, including arthropods such as ticks and insects, parasites, arachnids, and/or other arthropods, and ectoparasites and in general, viruses, bacteria and/or other microorganisms, are characterized primarily by a carrier (which can also be a mixture of carriers) having an absolute or resultant viscosity of from 100 to 1200, and especially greater than 120, S.U.S. (Saybolt Universal Seconds @ 100 degrees F.), with a pesticide, namely an insecticide, ectoparasitide, insect or other arthropod growth regulator (IGR), viricide, bacteriacide, and/or bacteriostatic compound (i.e. a compound that would create a bacteriostatic condition) being blended with the carrier to form the inventive mixture. This mixture does not operate systemically, and should not contain a surfactant or any type of emulsifier or emulsifying agent, which would tend to make the mixture more prone to absorption and/or soluble with water that strikes the animal, and hence unsuitable for its purpose. In particular, the mixture contains essentially no surfactant, emulsifier, or emulsifying agent, either in solution or in suspension. This lack of surfactant or emulsifier distinguishes the inventive mixture from prior known products.

The mixture of the present invention is intended for application to an animal to protect the animal against the effects of pests, for example by killing or repelling them, or otherwise counteracting their effects. Furthermore, the inventive mixture, with the proper active ingredient(s) incorporated therein, can, when applied to an animal, regulate the growth of any of the aforementioned organisms, and/or can interrupt, interdict, or prevent their breeding or ovipositing cycle.

The critical feature of the inventive mixture is a carrier having in particular a viscosity greater than 120, especially 350 to 650 S.U.S. The presently contemplated carrier is mineral oil, including vegetable oil, in the stated viscosity range. One specific example of a suitable mineral oil is DuoPrime 350, which is manufactured by the Citgo Company. This mineral oil has a viscosity of approximately 350 S.U.S. Other carriers, especially inert oil-based carriers, could also be utilized, as long they were greater than 120 S.U.S., whereby an effective midrange viscosity would be 220-750 S.U.S., with the presently preferred range being 350 to 650 S.U.S.

The inventive mixture includes a carrier that is chemically and/or physically inert relative to the pesticide, for example having physical properties that are compatible with those of the pesticide.

The mixture of the present invention has a number of advantages. For example, in the case of insecticides, insect or other arthropod growth regulators (IGRs) and ectoparasitides, the mixture ensures that the carrier, and hence the active ingredient blended therein, essentially lay on top of an animal's coat of hair, thereby making the active ingredient easily transmissible to flies, lice, other parasites or insects, arachnids, and/or other arthropods, and ectoparasites and in general, viruses, bacteria and/or other microorganisms when they land or are deposited on the animal. This is critical to ensuring a more efficient and more effective killing of target pests. Furthermore, since the active ingredient to a large extent resides on top of the hair rather than below the hair and on the skin of the animal, i.e. does not operate systemically, the potential for transdermal absorption of the active ingredients into the body of the animal is minimized. This in turn minimizes or prevents contamination of the human food chain or other animals' food chain for which the treated animal's products may be intended.

Another advantage of the present invention is that since the carrier of the inventive mixture has sufficient weight and mass when it is dispensed, for example by misting or spraying, not only will the proper spray pattern be achieved to adequately cover the target animal, but the adverse effects of wind are minimized. By way of example only, one suitable means for applying the inventive mixture is described in U.S. Pat. No. 6,230,660. The inventive mixture can also be applied in the form of a stream, and can be applied indirectly as well as by the direct methods indicated.

As indicated previously, the inventive carrier viscosity range maximizes keeping the mixture of the present invention on the surface of an animal, minimizing penetration below the hairline. This is important for ensuring that a target organism or pest comes into contact with the active ingredient of the mixture merely by landing on a treated animal. This overcomes the drawback of prior known mixtures, which penetrate below the outer layer of an animal's hair, so that a target organism is less likely to come into contact with the active ingredient. Although such a surface application exposes the mixture of the present invention to UV light, this is not a disadvantage because the mixture can be applied frequently enough on a routine basis, particularly with the equipment covered in the aforementioned patent, since this system is automated and precludes the need for labor inputs associated with application of the mixture.

A carrier within the viscosity range of the present invention also minimizes mechanical water migration loss of active ingredient during rainstorms or in situations where the animals are dosed with water either for cooling or cleaning them.

The inventive carrier viscosity range has the further advantage that the carrier itself tends to impart a physical "kill" mechanism. In particular, for example, flies pick up the carrier on their feet when they come into contact with the mixture. As the flies then "groom" themselves, they spread the oil over their air ducts and lungs and the flies suffocate because the mineral oil film that they deposit prevents the transfer of oxygen. Therefore, death can occur independently of the active ingredient.

One disadvantage of using the higher viscosity carriers as contemplated herein is that as ambient temperatures decrease, the flowability of the carrier decreases as well. This is significant particularly when the product is applied through an apparatus as contemplated in U.S. Pat. No. 6,230,660. In this instance, the flowability of the carrier may be insufficient to develop the optimum spray pattern required to adequately cover the target animal with compounds contemplated herein.

A way of overcoming this disadvantage is the addition of a volatile compound to the carrier, which compound is also soluble in or miscible with the carrier. Such addition would lower the overall viscosity of the carrier so long as it was in its closed container or within the delivery tubing between the pump and the nozzle, ensuring that the flowability required to generate the proper spray pattern is maintained. Once applied however, the volatile compound would evaporate thus returning the carrier to the absolute or resultant viscosity range(s) contemplated herein.

The insecticide, ectoparasitide, viricide, insect or other arthropod growth regulator (IGR), bacteriacide, and/or bacteriostatic compound of the inventive mixture can, for example, be a pyrethroid, including permethrin, pyrethrin and cinerin, an organophostate, or any other suitable active ingredient.

EXAMPLE 1

Pursuant to one specific example of the inventive mixture, the following were utilized:

|  | % Active by Weight. | % in Mix by Weight |
|---|---|---|
| Permethrin-Technical Grade | 97.70% | 1.024% |
| Piperonyl Butoxide-Technical | 99.98% | 1.000% |
| Mineral Oil (*DuoPrime 350 or Equiv*) + Other Inerts |  | 97.976% |
| Total |  | 100.00% |

After the appropriate batch size was determined, the technical grade Permethrin was heated to 140° F. for six to eight hours and was lightly agitated. The Permethrin was then thoroughly blended with the Piperonyl Butoxide. The resulting solution was then mixed with white mineral oil having a viscosity of 300 to 375 S.U.S.; the mixture was vigorously stirred to achieve uniform blending. The mixture was then ready for packaging or application to an animal that was to be treated, for example by being sprayed or misted onto the animal.

EXAMPLE 2

Pursuant to one specific example of the inventive mixture, the following were utilized:

|  | % Active by Weight. | % in Mix by Weight |
|---|---|---|
| Permethrin-Technical Grade | 97.70% | 0.512% |
| Piperonyl Butoxide-Technical | 99.98% | 1.000% |
| Mineral Oil (*DuoPrime 350 or Equiv*) + |  | 98.488% |

-continued

|  | % Active by Weight. | % in Mix by Weight |
|---|---|---|
| Other Inerts |  |  |
| Total |  | 100.00% |

EXAMPLE 3

Pursuant to one specific example of the inventive mixture, the following were utilized:

|  | % Active by Weight. | % in Mix by Weight |
|---|---|---|
| Permethrin-Technical Grade | 97.70% | 0.512% |
| Piperonyl Butoxide-Technical | 99.98% | 0.500% |
| Mineral Oil (DuoPrime 350 or Equiv) + Other Inerts |  | 98.988% |
| Total |  | 100.00% |

Pursuant to the present invention, it is also optionally possible to incorporate a light reflective compound within the inventive mixture, for example to aid in preventing overheating of an animal. Suitable reflective compounds that can be added to the inventive mixture include, by way of example only, zinc oxide and titanium dioxide. Furthermore, in order to extend the life of the inventive mixture after its application to the animal, it is optionally also possible to incorporate UV blockers and/or absorbers into the mixture. Such an additive or inhibitor can be zinc oxide or titanium dioxide, although for this use the particle size may have to be smaller than is the case for the light reflective compound in order to achieve optimal results. Such smaller particles could be incorporated within the mixture in combination with larger particles of the same or another component, thereby optimizing both light reflective and UV blocking and/or absorbing properties of the mixture.

The present invention is, of course, in no way restricted to the specific disclosure of the specification and examples, but also encompasses any modifications within the scope of the appended claims.

We claim:

1. A mixture for application on an animal, to provide barrier protection against pests, comprising:
   a carrier or combination of carriers that includes an oil-based carrier and that at least after application has an absolute or resultant viscosity of from 300 to 650 S.U.S.; and
   at least one pesticide with said carrier or combination of carriers, wherein said pesticide is adapted to act non-systemically relative to a host animal.

2. A mixture according to claim 1, wherein said mixture contains essentially no surfactant, emulsifier, or emulsifying agent, either in solution or in suspension 3. A mixture according to claim 1, wherein said oil-based carrier is mineral oil.

4. A mixture according to claim 1, wherein said carrier or combination of carriers is inert relative to said pesticide.

5. A mixture according to claim 1, that further includes a compound that has at least one of the properties of being light reflective, and ultraviolet blocking or absorptive.

6. A mixture according to claim 1, wherein said at least one pesticide is selected from the group consisting of pyrethroids and organophosphates.

7. A mixture according to claim 6, wherein said at least one pesticide is permethrin or pyrethrin.

8. A mixture according to claim 1, which further includes a volatile compound that is soluble in or miscible with said carrier or combination of carriers, wherein upon application to an animal said volatile compound evaporates to such an extent that said absolute or resultant viscosity is obtained.

9. A method of protecting an animal against pests, said method including the steps of:
   providing a carrier, or combination of carriers, that includes an oil-based carrier and that at least after an application has an absolute or resultant viscosity of from 100 to 1200 S.U.S.;
   mixing at least one of a non-systemically operating insecticide, ectoparasitide, viricide, insect or other arthropod growth regulator (IGR), bacteriacide, and bacteriostatic compound with said carrier to provide a mixture; and
   applying said mixture to an animal.

10. A method according to claim 9, wherein said mixture contains essentially no surfactant, emulsifier or emulsifying agent, either in solution or in suspension.

11. A method according to claim 9, wherein said step of applying comprises misting, spraying or pouring said mixture directly onto an animal.

12. A method according to claim 9, wherein said viscosity is greater than 120 S.U.S.

13. A method according to claim 12, wherein said viscosity is 300 to 650 S.U.S.

14. A method according to claim 9, wherein said mixture further includes a compound that has at least one of the properties of being light reflective, and ultraviolet blocking or absorptive.

15. A method according to claim 9, which includes the further step of adding to said carrier or combination of carriers a volatile compound that is soluble in or miscible therewith, wherein upon application to an animal said volatile compound evaporates to such extent that said absolute or resultant viscosity is obtained.

16. A method according to claim 12, wherein said viscosity is greater than 220 S.U.S.

* * * * *